(12) United States Patent
Rogan et al.

(10) Patent No.: US 11,160,940 B2
(45) Date of Patent: Nov. 2, 2021

(54) AEROSOL GENERATION SYSTEM WITH REPLACEABLE ATOMIZER

(71) Applicant: JT International S.A., Geneva (CH)

(72) Inventors: Andrew Robert John Rogan, Forres Grampian (GB); Frederick Waldern, Zurich (CH); Ralf Inauen, Zurich (CH)

(73) Assignee: JT International S.A.

(*) Notice: Subject to any disclaimer, the term of this patent is extended or adjusted under 35 U.S.C. 154(b) by 120 days.

(21) Appl. No.: 16/617,820

(22) PCT Filed: May 29, 2018

(86) PCT No.: PCT/EP2018/064068
§ 371 (c)(1),
(2) Date: Nov. 27, 2019

(87) PCT Pub. No.: WO2018/219949
PCT Pub. Date: Dec. 6, 2018

(65) Prior Publication Data
US 2020/0187562 A1    Jun. 18, 2020

(30) Foreign Application Priority Data
Jun. 2, 2017 (EP) ..................... 17174183

(51) Int. Cl.
*A24F 11/00* (2006.01)
*A24F 47/00* (2020.01)
(Continued)

(52) U.S. Cl.
CPC ............ *A61M 15/06* (2013.01); *A24F 40/40* (2020.01); *A24F 40/485* (2020.01); *A24F 40/10* (2020.01); *A24F 40/60* (2020.01)

(58) Field of Classification Search
CPC .......... A24F 40/10; A24F 40/40; A24F 40/42; A24F 40/485; A24F 40/60
(Continued)

(56) References Cited

U.S. PATENT DOCUMENTS

2013/0319407 A1    12/2013   Liu
2015/0007836 A1*   1/2015    Li .................. A24F 40/485
                                              131/329
(Continued)

FOREIGN PATENT DOCUMENTS

KR    20140002296 U    4/2014
WO    2016033741 A1    3/2016
WO    2016045076 A1    3/2016

OTHER PUBLICATIONS

International Search Report including Written Opinion for PCT/EP2018/064068 dated Jul. 31, 2018.

*Primary Examiner* — Hae Moon Hyeon
(74) *Attorney, Agent, or Firm* — Lerner, David, Littenberg, Krumholz & Mentlik, LLP

(57) ABSTRACT

An electrically operated aerosol generation system has a replaceable atomizer. The system includes a housing and an atomizer that can be received within a bore in a grasp ring of the housing. A power supply unit can be connected to the housing. A reservoir contains vaporizable liquid which can be supplied to the atomizer. A mouthpiece assembly is provided and can be actuated relative to the housing in order to separate and eject the atomizer from the housing when the power supply unit is removed.

21 Claims, 4 Drawing Sheets

(51) Int. Cl.
*A24F 40/485* (2020.01)
*A61M 15/06* (2006.01)
*A24F 40/40* (2020.01)
*A24F 40/10* (2020.01)
*A24F 40/60* (2020.01)

(58) Field of Classification Search
USPC .................................................. 131/328, 329
See application file for complete search history.

(56) References Cited

U.S. PATENT DOCUMENTS

| | | |
|---|---|---|
| 2016/0345629 A1 | 12/2016 | Mironov |
| 2017/0156408 A1* | 6/2017 | Li .............................. H05B 3/16 |
| 2017/0196266 A1 | 7/2017 | Chen |
| 2017/0273359 A1 | 9/2017 | Liu |
| 2018/0000156 A1* | 1/2018 | Qiu .......................... A24F 40/40 |
| 2020/0146351 A1* | 5/2020 | Rogan .................... A24F 40/485 |

* cited by examiner

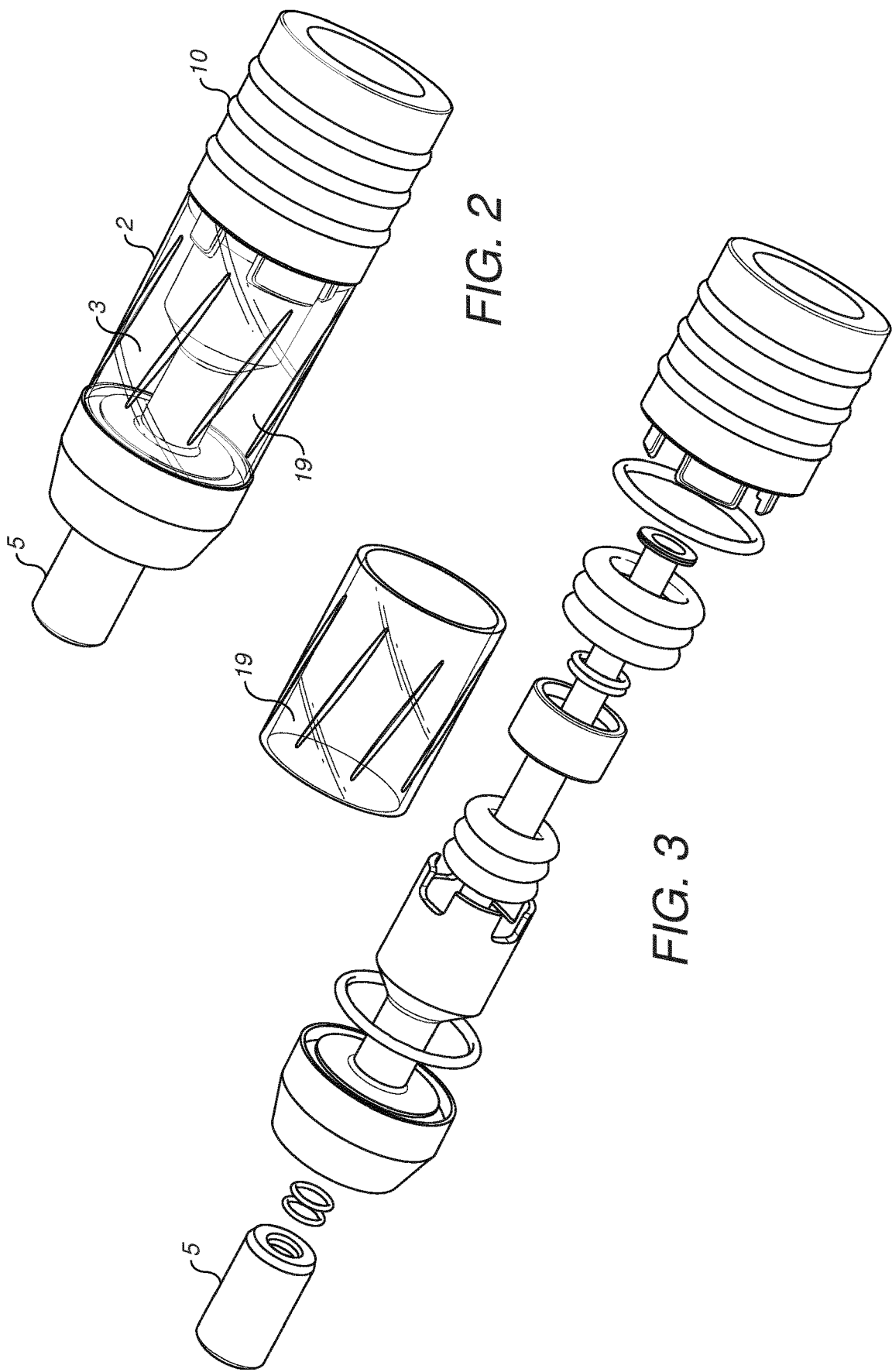

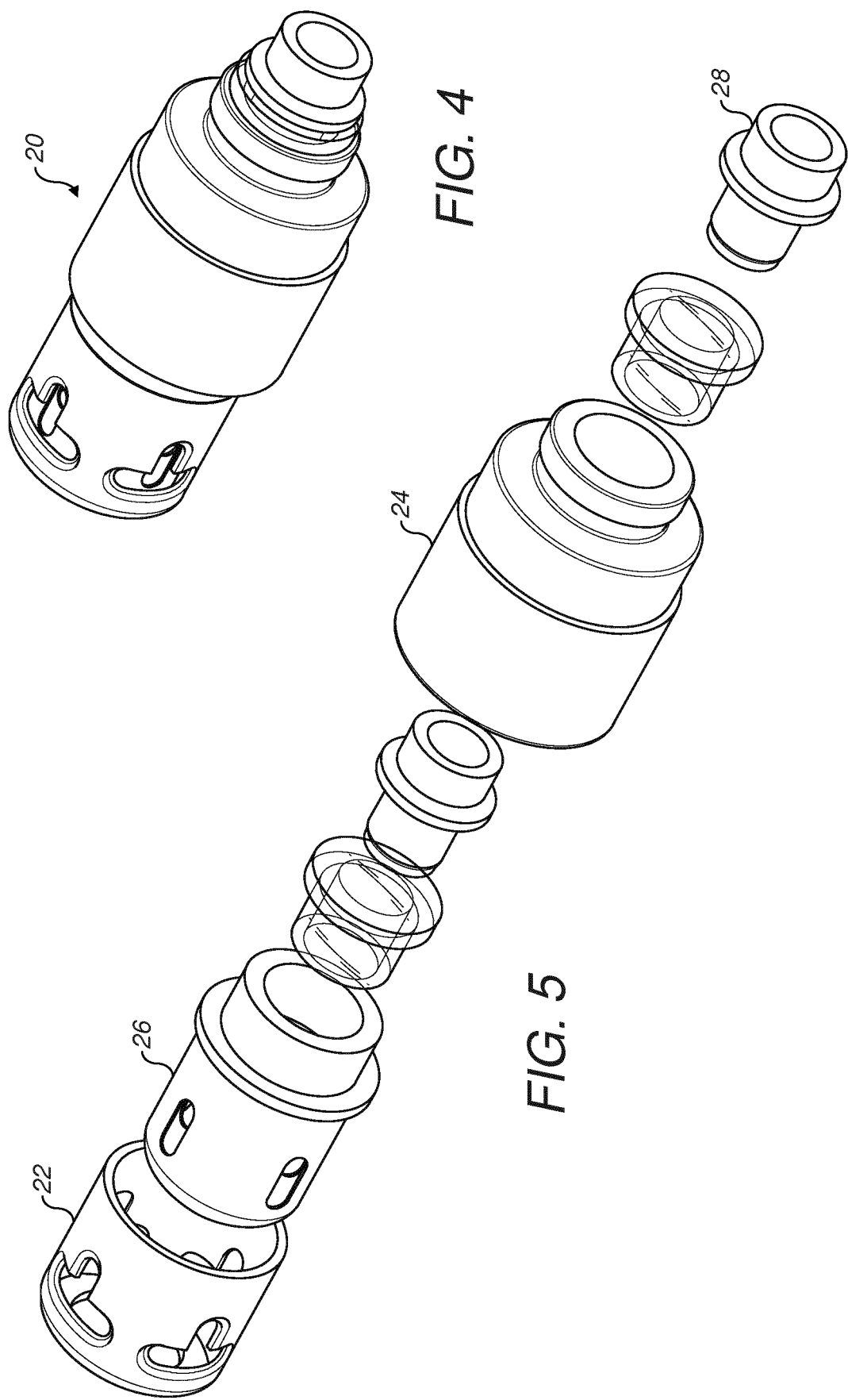

AEROSOL GENERATION SYSTEM WITH REPLACEABLE ATOMIZER

CROSS-REFERENCE TO RELATED APPLICATIONS

The present application is a national phase entry under 35 U.S.C. § 371 of International Application No. PCT/EP2018/064068, filed May 29, 2018, published in English, which claims priority to European Patent Application No. 17174183.8 filed Jun. 2, 2017, the disclosures of which are incorporated herein by reference.

BACKGROUND OF THE INVENTION

The present invention relates to an electrically operated aerosol generation system such as an electronic cigarette.

Electronic cigarettes and other aerosol inhalers are becoming increasingly popular consumer products. In these products an aerosol forming substance is stored in a tank in liquid form and is supplied to an atomizer which can generate an aerosol. The atomizer includes an absorbent material and a heating coil that vaporises the liquid aerosol forming substance. A battery is connected to the atomizer, which is typically operated by a button or an air pressure sensor. Air inlets are provided so that the user can draw air into the device through or past the atomizer. In use, a user activates the atomizer and inhales the aerosol that is generated, using a mouthpiece.

Sometimes it becomes necessary to replace an atomizer. This may be necessary if the atomizer heating coil becomes degraded. In conventional designs it can be difficult to access the atomizer in order to fit a replacement. Additionally, the atomizer can become hot in use, which means that a user may need to wait for the components to cool before trying to fit a replacement. A further difficulty is that the atomizer may have liquid from the tank on or in it. Thus, with conventional designs a user may be brought into direct contact with the liquid aerosol forming substance when attempting to remove a used atomizer, which is undesirable.

BRIEF SUMMARY OF THE INVENTION

According to an aspect of the invention there is provided an electrically operated aerosol generation system, comprising: a housing; an atomizer that can be received by the housing; a reservoir configured to supply vaporisable liquid to the atomizer; a mouthpiece assembly which is actuatable relative to the housing in order to eject the atomizer; and a power supply unit configured for connection with the housing.

In this way, the mouthpiece assembly can be used as a mechanical ejector for the atomizer, which can be slid out of the housing. The atomizer can therefore be replaced easily. A user does not need to physically touch the spent atomizer, which is advantageous because it may be hot and/or have vaporisable liquid residue on it.

Preferably the atomizer is slidably received in the housing, and is held in place by frictional engagement, a press fit or an interference fit. In one arrangement the atomizer may be held in the housing by one or more o-rings. The grip of the o-rings on the atomizer may be reduced when the atomizer is pushed out of the housing by the mouthpiece assembly.

The mouthpiece assembly may be arranged to actuate the atomizer between an operative position in which vaporisable liquid can be supplied to the atomizer from the reservoir, and an inoperative position in which vaporisable liquid cannot be supplied to the atomizer from the reservoir. In the operative position vapour generated by the atomizer may be transmitted to the mouthpiece assembly along an airflow path. The atomizer may be ejected from the housing in the inoperative position. Advantageously this can allow removal of the atomizer while minimising any leakage of vaporisable liquid from the reservoir.

The mouthpiece assembly may be in an extended position when the atomizer is received in the housing and the mouthpiece assembly may be in a retracted position when the atomizer is ejected from the housing. Once an old atomizer has been removed, a replacement atomizer may be introduced to the housing. This may cause the mouthpiece assembly to return to its extended position, ready for use.

The mouthpiece assembly may be configured to close or to block a flow path between the atomizer and the reservoir in the inoperative position. In one arrangement the mouthpiece may comprise a sealing portion which closes or blocks the flow path.

Preferably the connection between the power supply unit and the housing inhibits actuation of the mouthpiece assembly. Therefore, the power supply unit may need to be detached from the housing before the mouthpiece assembly can be actuated and the atomizer can be ejected. A threaded or bayonet connection may be provided between the power supply unit and the housing.

A viewing window may be provided in the housing for a user to inspect the volume of vaporisable liquid in the reservoir. The housing may form part of the reservoir. In particular, the housing may form an outer wall of the reservoir. A transparent portion of the housing may be provided to allow a user to see whether the reservoir needs to be re-filled.

The mouthpiece assembly may comprise an elongate member having an airflow channel extending longitudinally thereof. In addition, the mouthpiece assembly may be configured for translational or sliding movement relative to the housing, when actuated.

In another arrangement the mouthpiece assembly may be configured for rotational movement, when actuated. In this configuration the user may twist the mouthpiece assembly. The twisting movement of the mouthpiece assembly may drive the atomizer longitudinally relative to the housing so that it becomes disattached.

According to another aspect of the invention there is provided a method of removing an atomizer in an electrically operated aerosol generation system, comprising a housing; an atomizer that can be received by the housing; a reservoir configured to supply vaporisable liquid to the atomizer; a mouthpiece assembly which is actuatable relative to the housing; and a power supply unit configured for connection with the housing, the method comprising the step of actuating the mouthpiece assembly relative to the housing in order to eject the atomizer from the housing. The method may involve disconnecting the power supply unit before actuating the mouthpiece assembly.

The method may involve replacing the atomizer, which includes a further step of introducing a further atomizer to the housing. The step of introducing the further atomizer to the housing preferably involves actuating the mouthpiece assembly and moving it from its retracted position to its extended position. The method may then involve re-attaching the power supply unit to the housing so that actuation of the mouthpiece assembly is inhibited.

BRIEF DESCRIPTION OF THE DRAWINGS

Embodiments of the invention are now described, by way of example, with reference to the drawings, in which:

FIG. 2 is a perspective view of the mouthpiece assembly and reservoir of the inhaler device shown in FIG. 1;

FIG. 3 is an exploded view of the mouthpiece assembly and reservoir shown in FIG. 2;

FIG. 4 is a perspective view of an atomizer in the inhaler device shown in FIG. 1;

FIG. 5 is an exploded view of the atomizer shown in FIG. 4;

DETAILED DESCRIPTION

With reference to the Figures, an inhaler device 100 in the form of a personal vaporizer device (also known as an electronic smoking article or an "e-cigarette") according to a preferred embodiment is illustrated.

Figure 6:
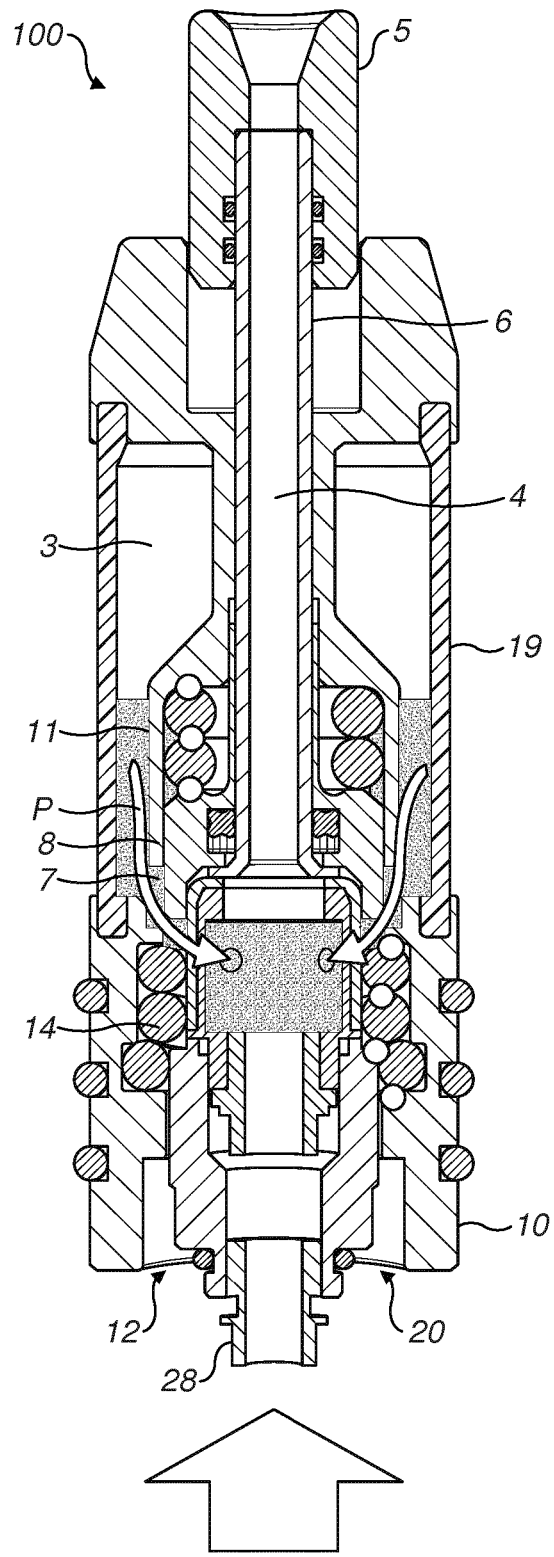
FIG. 6 is a cross-sectional side view of an electrically operated aerosol generation system in an operative configuration, in an embodiment of the invention.
Figure 7:
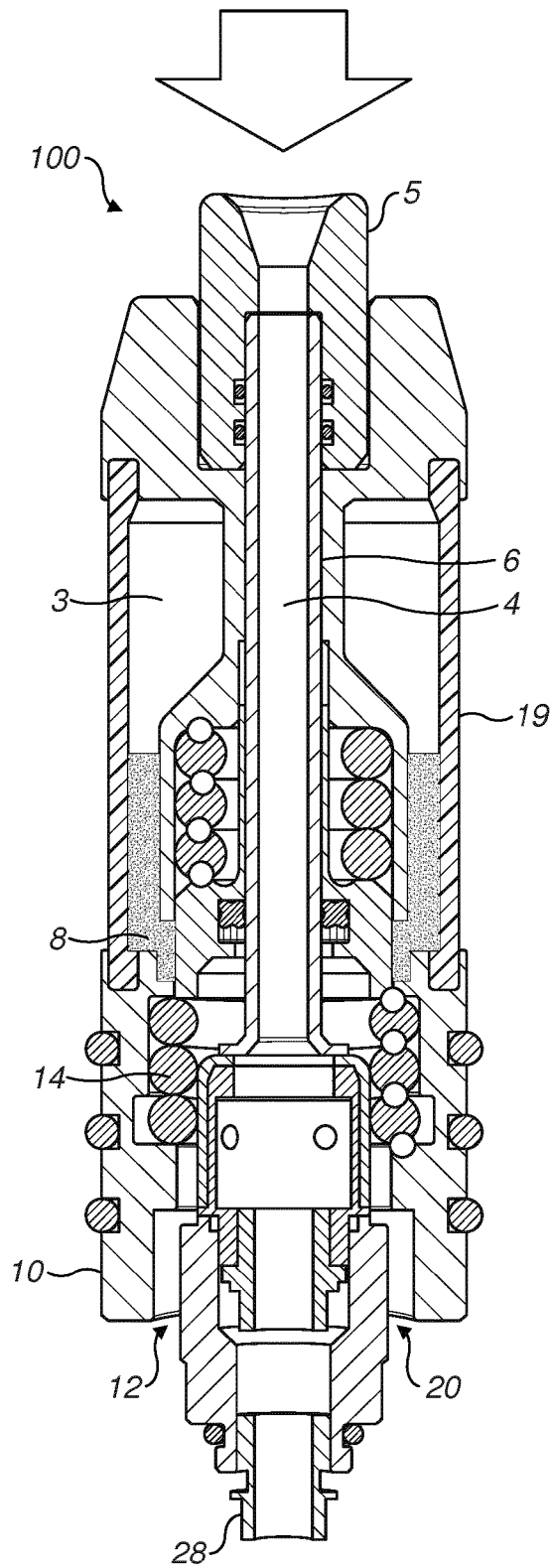
FIG. 7 is another cross-sectional side view of the electrically operated aerosol generation system shown in FIG. 6, but in an inoperative configuration.

The personal vaporizer device or e-cigarette 100 is generally elongate and has a substantially circular cylindrical shape. The e-cigarette 100 comprises a housing 2 which encloses a reservoir 3 for storing a liquid to be vaporized. The reservoir 3 has a generally annular form and surrounds a central core 4 of the housing 2. The mouthpiece includes a longitudinal member 6 as an elongate member which fits within the central core 4. The longitudinal member 6 is slideable within the central core 4 and is shown in FIGS. 6 and 7 to have an airflow channel extending longitudinally thereof for conveying vapour formed from the liquid to a mouth of a user. The housing 2 includes a transparent window 19 in an outer wall of the reservoir 3 so that a user can see how much liquid is present.

The housing 2 is connected to a power supply unit 30 which stores electrical potential or energy, e.g. in one or more batteries, enclosed within a cylindrical casing 31 of that unit 30. The power supply unit 30 is provided for delivering electrical power to an atomizer 20.

The mouthpiece 5 is configured for movement between an extended position (as shown in FIG. 6) and a retracted position (as shown in FIG. 7). A flow path P is provided for the liquid from the reservoir 3 to travel to the atomizer 20 where it can be vaporized. The flow path P includes one or more outlet ports 7 formed in a wall 11 of the reservoir 3, through which the liquid may flow under gravity and/or via capillary action (e.g. in the event of a narrow channel being provided) along the path P in the direction of the arrows towards the atomizer 20. The mouthpiece 5 includes a valve part or sealing part 8 which can block the outlet port 7 when the mouthpiece 5 is retracted. It is to be appreciated that a wall 11 of the central core 4 also constitutes the wall 11 of the reservoir 3 in which the outlet ports 7 are formed.

In one arrangement a spring (not shown) may be provided to bias the mouthpiece 5 in its retracted configuration. However, in the embodiment shown the mouthpiece 5 is not biased, and must be actuated manually.

A grasp ring 10 is provided adjacent the transparent window 19. The grasp ring 10 can be used to hold the e-cigarette 100 in normal use. Also, a user can hold the grasp ring 10 while actuating the mouthpiece 5.

Figure 1:
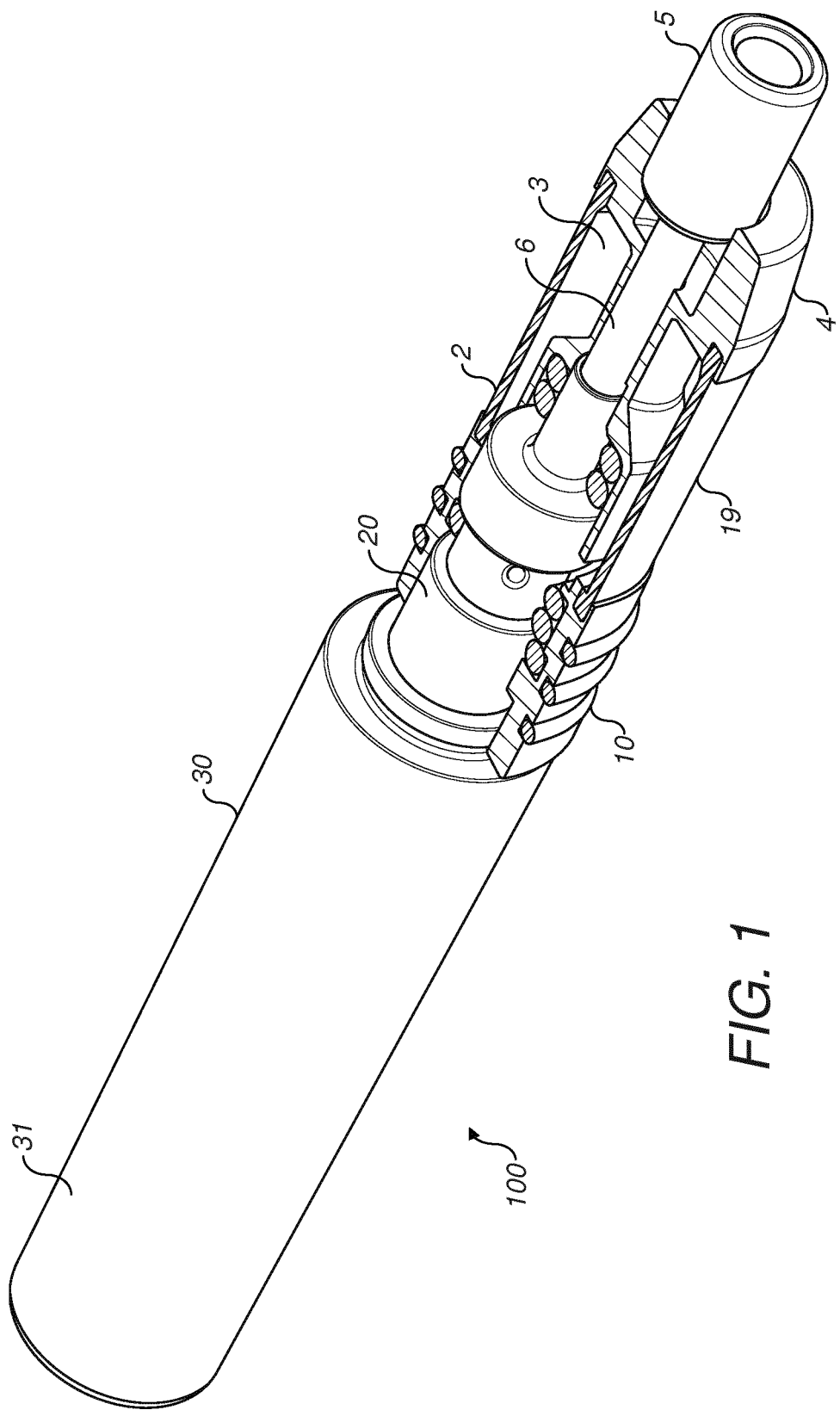
FIG. 1 is a perspective view of an inhaler device, part of which is shown as a cross-section in an embodiment of the invention.

The base of the grasp ring 10 is internally threaded (not shown). The power supply unit 30 includes an external thread, which can be connected to the internal thread of the grasp ring 10. In this way, the power supply unit 30 can be connected to the housing 2. In other arrangements a bayonet connection or a clip can be provided to create a secure connection. With the power supply unit 30 connected to the housing 2 (as shown in FIG. 1) an upper wall of the power supply unit 30 abuts a lower surface of the atomizer 20. This arrangement effectively locks the mouthpiece 5 in its extended configuration. The mouthpiece 5 cannot therefore be actuated when the power supply unit 30 is connected to the housing 2.

The atomizer 20 includes a number of component parts. The aerosol generator 26 is provided within a lower atomizer sleeve 22. The lower atomizer sleeve 22 is connected to an upper atomizer sleeve 24, which has a slightly larger radius. An electrical connector 28 is provided at one end of the atomizer 20, adjacent the upper atomizer sleeve 24, for connection to the power supply unit 30. In FIGS. 6 and 7 the upper atomizer sleeve 24 is depicted below the lower atomizer sleeve 22.

In use, the atomizer 20 is received within an internal bore 12 of the grasp ring 10. The internal bore 12 contains a number of o-rings 14 which have an internal radii that are slightly smaller than the respective external radii of the lower atomizer sleeve 22 and the upper atomizer sleeve 24. The frictional engagement between the o-rings 14 and the sleeves 22, 24 is enough to hold the atomizer 20 securely in place when the mouthpiece is in its extended position and the atomizer 20 is fully received in the bore 12.

With the atomizer 20 installed in the grasp ring 10, the lower end of the longitudinal member 6 abuts the atomizer 20, adjacent the lower sleeve 22. As illustrated in FIGS. 6 and 7, actuation of the mouthpiece 5 from the extended position to the retracted position causes the atomizer 20 to move downwards within the grasp ring 10. With the mouthpiece 5 in its fully retracted position, as shown in FIG. 7, the o-rings 14 that were previously in contact with the upper atomizer sleeve 24 are now positioned adjacent the lower atomizer sleeve 22. The lower atomizer sleeve 22 has a smaller radius than the upper atomizer sleeve 24, and therefore the o-rings 14 have a much looser grip on the atomizer 20 in this configuration. In preferred embodiments the gripping force between the o-rings 14 and the lower atomizer sleeve 22 is less than the force of gravity that acts on the atomizer 20. Thus, the atomizer 20 can simply drop out of the grasp ring 10 when the mouthpiece 5 is depressed. This can allow a user to eject the atomizer 20 without touching it directly. This is advantageous because the atomizer 20 may be hot immediately after use. In addition, the atomizer 20 may have liquid residue on it from the reservoir 3, which it is preferable for the user to avoid.

In order to remove the atomizer 20 the user must first unscrew and remove the power supply unit 30 from the housing 2. The user can then actuate the mouthpiece 5 by moving it from the extended position to the retracted position. This slides the atomizer 20 relative to the grasp ring 10 so that it can drop out of the open end. A fresh atomizer 20 can then be introduced into the internal bore 12 of the grasp ring 10. An upper surface of the fresh atomizer 20 introduced to the grasp ring 10 acts on a lower surface of the longitudinal member 6. Thus, sliding a fresh atomizer 20 into the grasp ring 10 can cause the mouthpiece 5 to move from its retracted position into its extended position. The power supply unit 30 can then be re-attached so that the e-cigarette 100 is ready for use.

Advantageously the valve 8 isolates the liquid in the reservoir 3 from the atomizer 20 when the mouthpiece 5 is in its retracted position. Therefore, a used atomizer 20 can be ejected and replaced without any liquid leaking from the reservoir 3.

The invention claimed is:

1. An electrically operated aerosol generation system, comprising:
   a housing;
   an atomizer that can be received by the housing;
   a reservoir in the housing configured to supply vaporisable liquid to the atomizer;
   a mouthpiece assembly connected to the housing and which is actuatable relative to the housing in order to eject the atomizer from the housing; and
   a power supply unit configured for connection with the housing.

2. The electrically operated aerosol system of claim 1, wherein the atomizer is slidably received in the housing, and is held in place by frictional engagement.

3. The electrically operated aerosol system of claim 1, wherein the mouthpiece assembly is arranged to actuate the atomizer between an operative position in which vaporisable liquid can be supplied to the atomizer from the reservoir, and an inoperative position in which vaporisable liquid cannot be supplied to the atomizer from the reservoir.

4. The electrically operated aerosol system of claim 3, wherein the mouthpiece assembly is in an extended position when the atomizer is received in the housing and the mouthpiece assembly is in a retracted position when the atomizer is ejected from the housing.

5. The electrically operated aerosol system of claim 3, wherein the mouthpiece assembly is configured to close or to block a flow path between the atomizer and the reservoir in the inoperative position.

6. The electrically operated aerosol system of claim 5, wherein the mouthpiece assembly comprises a sealing portion which closes or blocks the flow path.

7. The electrically operated aerosol system of claim 1, wherein a connection between the power supply unit and the housing inhibits actuation of the mouthpiece assembly.

8. The electrically operated aerosol system of claim 1, further comprising a viewing window in the housing for a user to inspect the volume of vaporisable liquid in the reservoir.

9. The electrically operated aerosol system of claim 1, wherein the mouthpiece assembly comprises an elongate member having an airflow channel extending longitudinally thereof.

10. The electrically operated aerosol system of claim 1, wherein the mouthpiece assembly is configured for rotational movement, when actuated.

11. The electrically operated aerosol system of claim 1, wherein the mouthpiece assembly is configured for translational or sliding movement relative to the housing, when actuated.

12. The electrically operated aerosol system of claim 11, wherein the atomizer is slidably received in the housing, and is held in place by frictional engagement.

13. The electrically operated aerosol system of claim 11, wherein the mouthpiece assembly is arranged to actuate the atomizer between an operative position in which vaporisable liquid can be supplied to the atomizer from the reservoir, and an inoperative position in which vaporisable liquid cannot be supplied to the atomizer from the reservoir.

14. The electrically operated aerosol system of claim 13, wherein the mouthpiece assembly is in an extended position when the atomizer is received in the housing and the mouthpiece assembly is in a retracted position when the atomizer is ejected from the housing.

15. The electrically operated aerosol system of claim 13, wherein the mouthpiece assembly is configured to close or to block a flow path between the atomizer and the reservoir in the inoperative position.

16. The electrically operated aerosol system of claim 15, wherein the mouthpiece assembly comprises a sealing portion which closes or blocks the flow path.

17. The electrically operated aerosol system of claim 11, wherein a connection between the power supply unit and the housing inhibits actuation of the mouthpiece assembly.

18. The electrically operated aerosol system of claim 11, further comprising a viewing window in the housing for a user to inspect the volume of vaporisable liquid in the reservoir.

19. The electrically operated aerosol system of claim 11, wherein the mouthpiece assembly comprises an elongate member having an airflow channel extending longitudinally thereof.

20. A method of removing an atomizer from an electrically operated aerosol generation system that includes a housing, the atomizer that can be received by the housing, a reservoir in the housing configured to supply vaporisable liquid to the atomizer, a mouthpiece assembly connected to the housing and which is actuatable relative to the housing, and a power supply unit configured for connection with the housing, the method comprising the step of:
   actuating the mouthpiece assembly relative to the housing in order to eject the atomizer from the housing.

21. The method of claim 20, further comprising the step of disconnecting the power supply unit before actuating the mouthpiece assembly.

* * * * *